(12) United States Patent
Mazzone

(10) Patent No.: US 7,155,422 B2
(45) Date of Patent: Dec. 26, 2006

(54) MEDICAL INFORMATION SYSTEM, METHOD AND ARTICLE OF MANUFACTURE

(76) Inventor: Thomas Mazzone, 3200 E. Blood Rd., Cowlesville, NY (US) 14037

( * ) Notice: Subject to any disclaimer, the term of this patent is extended or adjusted under 35 U.S.C. 154(b) by 434 days.

(21) Appl. No.: 09/932,371

(22) Filed: Aug. 17, 2001

(65) Prior Publication Data

US 2002/0023063 A1 Feb. 21, 2002

Related U.S. Application Data

(60) Provisional application No. 60/279,870, filed on Mar. 29, 2001, provisional application No. 60/226,401, filed on Aug. 18, 2000.

(51) Int. Cl.
*G06F 7/00* (2006.01)

(52) U.S. Cl. ............................. 706/50; 706/45; 705/3; 713/185

(58) Field of Classification Search ................. 706/50, 706/62, 924; 705/2; 707/9; 711/147, 163, 711/164; 726/2, 4, 5, 7, 27–29
See application file for complete search history.

(56) References Cited

U.S. PATENT DOCUMENTS

| | | | | |
|---|---|---|---|---|
| 5,077,666 A * | 12/1991 | Brimm et al. | ................. | 705/2 |
| 5,255,187 A * | 10/1993 | Sorensen | .................... | 600/300 |
| 5,280,527 A * | 1/1994 | Gullman et al. | ............. | 713/184 |
| 5,301,258 A * | 4/1994 | Hayashi | ....................... | 706/52 |
| 5,341,291 A * | 8/1994 | Roizen et al. | ............... | 600/300 |
| 5,623,637 A * | 4/1997 | Jones et al. | .................. | 711/164 |
| 5,661,668 A * | 8/1997 | Yemini et al. | .............. | 702/186 |
| 5,704,371 A * | 1/1998 | Shepard | ...................... | 128/897 |
| 5,771,291 A * | 6/1998 | Newton et al. | ............. | 713/185 |
| 5,845,255 A * | 12/1998 | Mayaud | ......................... | 705/3 |
| 5,899,998 A * | 5/1999 | McGauley et al. | ...... | 707/104.1 |
| 6,018,713 A * | 1/2000 | Coli et al. | ..................... | 705/2 |
| 6,026,363 A * | 2/2000 | Shepard | ......................... | 705/3 |
| 6,073,106 A * | 6/2000 | Rozen et al. | .................. | 705/3 |
| 6,082,776 A * | 7/2000 | Feinberg | ...................... | 283/72 |
| 6,226,620 B1 * | 5/2001 | Oon | ............................. | 705/2 |
| 6,249,755 B1 * | 6/2001 | Yemini et al. | .............. | 702/183 |
| 6,272,468 B1 * | 8/2001 | Melrose | ........................ | 705/2 |
| 6,278,999 B1 * | 8/2001 | Knapp | ........................... | 707/9 |
| 6,412,070 B1 * | 6/2002 | Van Dyke et al. | .......... | 713/200 |
| 6,463,417 B1 * | 10/2002 | Schoenberg | ................... | 705/2 |
| 6,488,205 B1 * | 12/2002 | Jacobson | ..................... | 235/380 |

OTHER PUBLICATIONS

Corcoran et al; Smart Cards and Biometrics; Linux Journal; Mar. 1999.*
Barrett et al; Automated Lesion Data Base Building for the Treatment of Retinal Disorders; IEEE International Conference Proceedings Image Processing; vol. 1; Nov. 13-16, 1994; pp. 426-430.*
Hagland; Smart Cards Knock at Healthcare's Door; Healthcare Informatics; Oct. 2000; pp. 77-82.*
Hagland, Smart Cards Knock at Healthcare's Door, Healthcare Informatics, Oct. 2000, pp. 77-82.

* cited by examiner

*Primary Examiner*—David Vincent
*Assistant Examiner*—Omar F. Fernandez Rivas
(74) *Attorney, Agent, or Firm*—Hodgson Russ LLP

(57) ABSTRACT

The invention includes a method, an article of manufacture and a system related to providing medical information and other information helpful in providing medical services.

38 Claims, 3 Drawing Sheets

MEDICAL INFORMATION SYSTEM, METHOD AND ARTICLE OF MANUFACTURE

CROSS CLAIM TO RELATED APPLICATION

This application claims priority to U.S. provisional patent application No. 60/279,870, filed Mar. 29, 2001. This application also claims priority to U.S. provisional patent application No. 60/226,401, filed Aug. 18, 2000.

BACKGROUND INFORMATION

The invention relates generally to providing medical information. The invention includes a system, a method and an article of manufacture related to providing medical information and other information helpful in providing medical services.

In an existing system of providing medical information, many different pieces of information may need to be collected, reviewed and analyzed. The information may include medical consultant summaries, hospitalization summaries, diagnostic reports and physician records. Traditionally, this information exists in paper form and has been difficult to gather for viewing in one location. Furthermore, each piece of information may be in a different format, thereby making it difficult for a person to quickly extract the information required.

BRIEF DESCRIPTION OF THE DRAWINGS

For a fuller understanding of the nature and objects of the invention, reference should be made to the following detailed description taken in conjunction with the accompanying drawings, in which.

DETAILED DESCRIPTION

Figure 1:
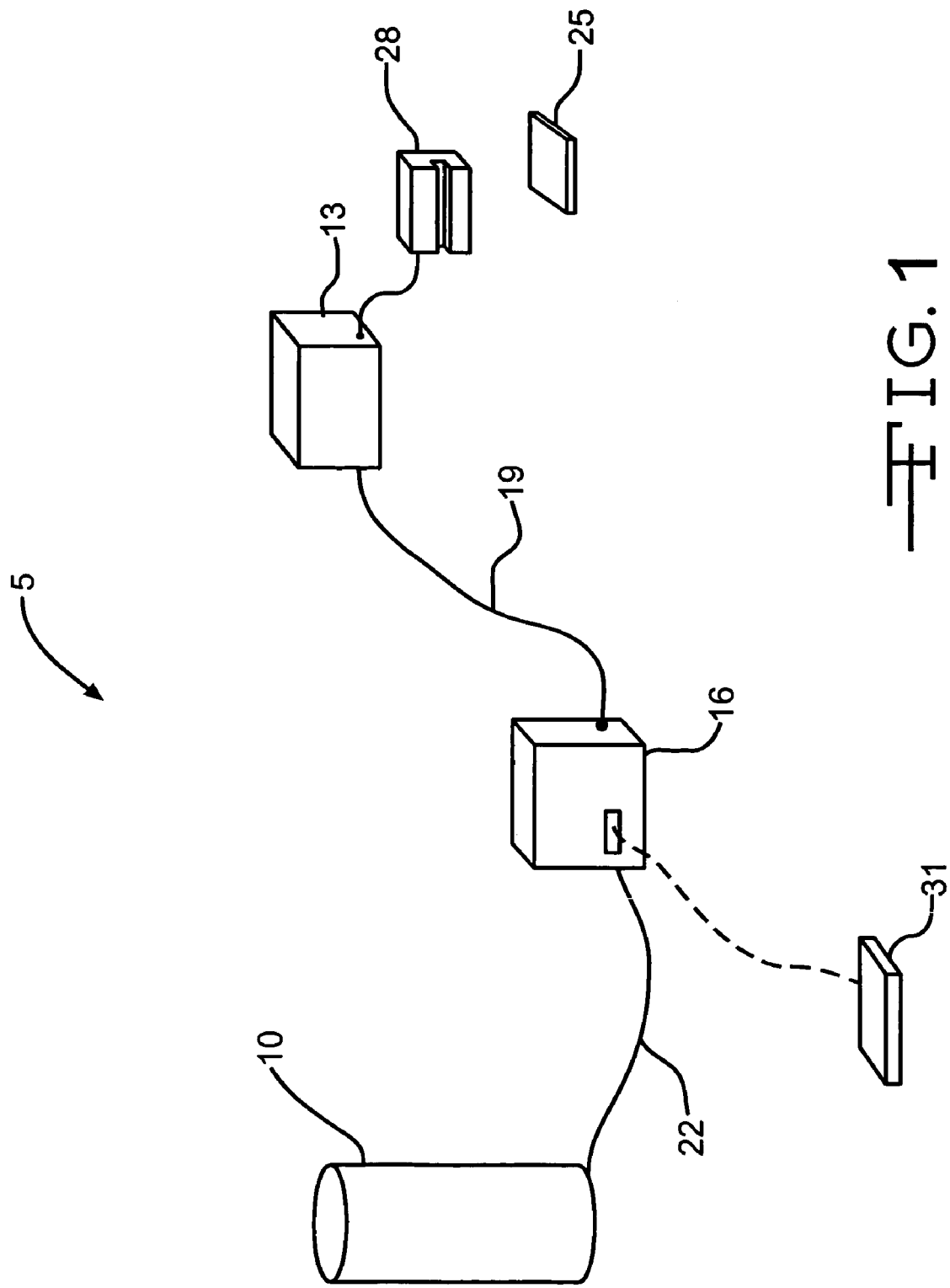
FIG. 1 is a diagram of a system according to the invention.

FIG. 1 illustrates a medical information system 5 according to the present invention. The system includes a database 10 of health information descriptions. A description may include a medical history related to a patient, an image of the patient's face, the patient's address, contact information, next of kin, a signed power of attorney consenting to certain medical treatment such as the patient's desires regarding emergency or life sustaining treatment, medical insurance information, employment information, preferences such as organ donor preferences, and blood type. The medical history portion of a description may include information about immunizations, surgeries, medical problems, allergies, current medications, laboratory test results and diagnostic test results. The health information descriptions may be in a standardized format. The health information descriptions may also be records of non-standardized documents that were scanned and then recorded in the database.

Access to the database 10 may be provided via a first computer 13 that is in communication with a second computer 16, for example via the Internet. The first computer 13 may be in communication with the second computer 16 via a first communication pathway 19. The second computer 16 may be in communication with the database 10 via a second communication pathway 22.

A description may be related to one or more associated pairs. An associated pair may include an associated access code and an associated password. The associated access code and the associated password each may be, for example, a series of characters issued by an operator of the system 5. Either code may be similar to a code issued by a medical organization, such as the American Medical Association, a government or chosen by the user. Either code may correspond to a fingerprint or retinal scan of the user.

The first computer 13 may be programmed to provide a prospective pair. A prospective pair may include a prospective access code and a prospective password. The second computer 16 may be programmed to determine whether a prospective pair corresponds to one of the associated pairs. If the prospective pair is determined to correspond to one of the associated pairs, then the second computer 16 may provide the description that corresponds to the prospective pair.

In order to accommodate a change to a description, the first computer 13 may be programmed to permit a user to enter the change and then provide the change. The second computer 16 may be programmed to receive the change, and then modify the database 10 to reflect the change. The second computer 16 may also be programmed to record who made the change. The system 5 may be made so that any changes are made only by certain users, for example, by a patient's primary care physician.

The system 5 may include a card 25 having a card code. The card code may correspond to the prospective access code the user desires to have provided by the first computer 13. For example, each patient, physician, health care provider and medical cost payer may have a card 25, each with a unique card code so the system 5 can determine which user is using the system 5. The card code may be an optically or magnetically scannable code that is unique to and identifies a user of the system 5. The card code may also be stored in a computer readable memory on the card 25, for example in a manner similar to a smart card. The system 5 may include a card reader 28 that reads the card code and provides the card code to the first computer 13. It should be noted that the system 5 may be implemented such that the card 25 has a device, such as a microcomputer, that requires entry of a card password prior to the card 25 providing the card code. The card password may be the same as the associated password referenced above, or may be another password.

In use, one of the associated pairs may be issued to one of the patients, and the description corresponding to that patient may be related in the database 10 to that associated pair. Then, when the patient's associated pair is provided, the description related to that patient will be provided by the system 5.

One of the associated pairs may be issued to a physician, and the descriptions corresponding to that physician's patients may be related in the database 10 to the physician's associated pair. Then, when the physician's associated pair is presented as a prospective pair, the physician may be provided with any of the descriptions of his/her patients.

One of the associated pairs may be issued to a health care provider, such as a hospital, and the descriptions corresponding to the health care provider's patients may be related in the database 10 to the health care provider's associated pair. Then, when the health care provider's associated pair is presented as a prospective pair, the health care provider may be provided with any of the descriptions of its patients.

One of the associated pairs may be issued to a medical cost payer, such as a medical insurance company. The descriptions corresponding to the medical cost payer's customers may be related in the database 10 to the medical cost payer's associated pair. Then, when the medical cost payer's associated pair is presented as a prospective pair, the medical cost payer may be provided with any of the descriptions of its customers.

In a variation of the embodiment described above, a patient's health information description may be accessed upon providing a prospective pair that includes a patient's associated access code and the password of another user, such as a physician, health care provider, or medical cost payer. In this manner, the patient need not disclose his/her password to another user in order to permit that other user to have access to the patient's description. Once the other user accesses the patient's description, that other user's associated pair may be related to the patient's description, thereby allowing that other user to access later the patient's description without using the patient's access code.

For example, if a patient arrives at a hospital and is unable to provide his/her password, but a hospital staff member discovers the patient's card 25, the hospital staff member may swipe the patient's card 25 through a card reader, and then the staff member may swipe the hospital's card 25 or the staff member's card 25 through the card reader. The system would then prompt the staff member for the password corresponding to the hospital's card 25 or the staff member's card 25, as the case may be. Upon entering the password, the staff member would be permitted access to the patient's information.

The system 5 may be made so that a message is sent to a patient, physician, health care provider, medical cost payer, or other individual when a description is provided. For example, the second computer 16 may be programmed to cause a message to be sent to one of the patients when the description relating to that patient is provided. The message may indicate who accessed the description, and may also indicate whether any changes were made, and if changes were made, what those changes are.

Figure 2:
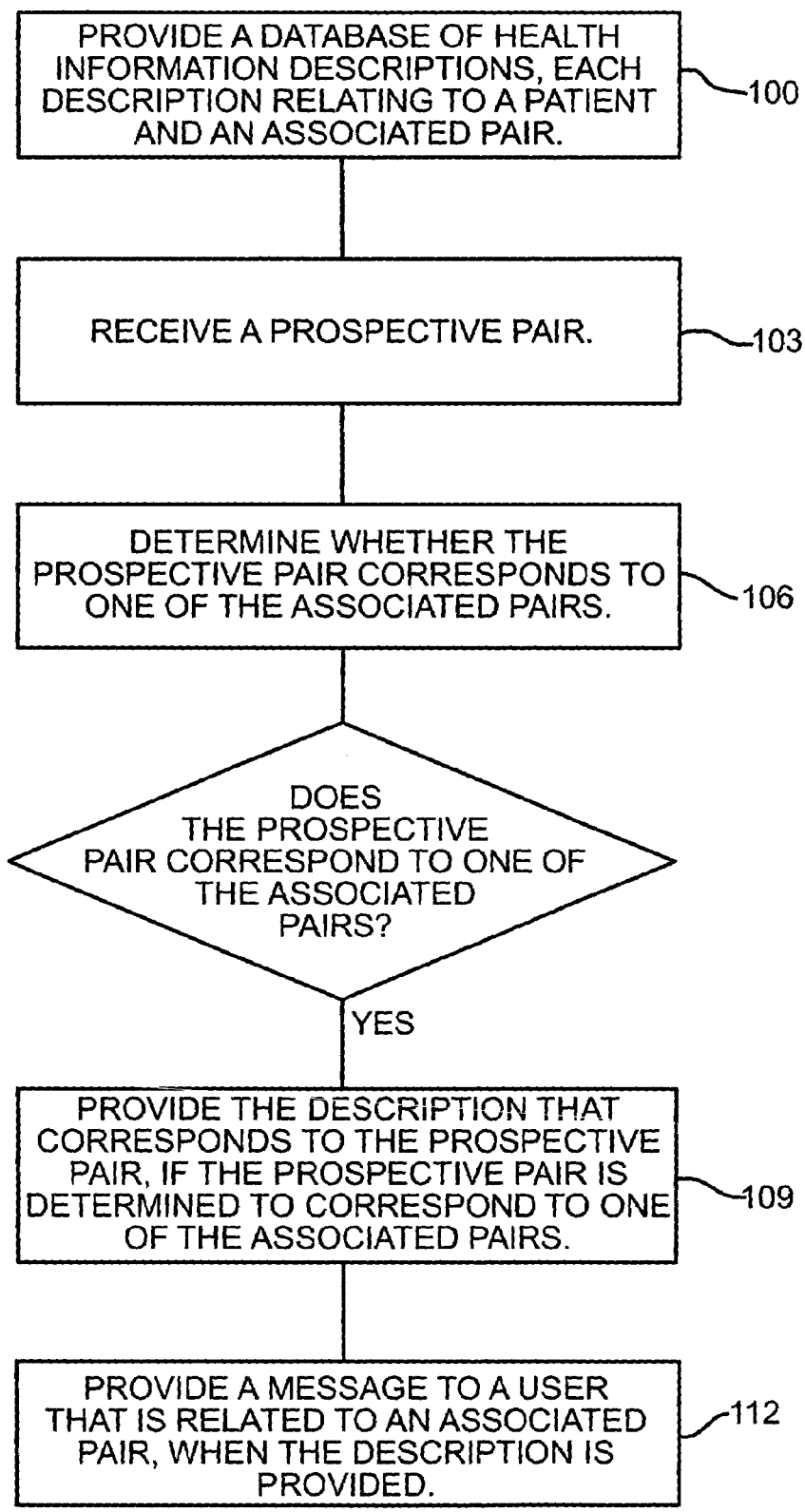
FIG. 2 is a flow chart illustrating a method according to the invention.

The invention may be implemented as a method. FIG. 2 illustrates a method according to the invention. In one such method, a database of health information descriptions is provided 100. Each description may relate to a patient and an associated pair. Each associated pair may comprise an associated access code and an associated password. A prospective pair, comprising a prospective access code and a prospective password, may be provided. If the provided prospective pair is received 103, a determination 106 may be made as to whether the prospective pair corresponds to one of the associated pairs. If the prospective pair is determined to correspond to one of the associated pairs, then the description that corresponds to the prospective pair may be provided 109.

Figure 3:
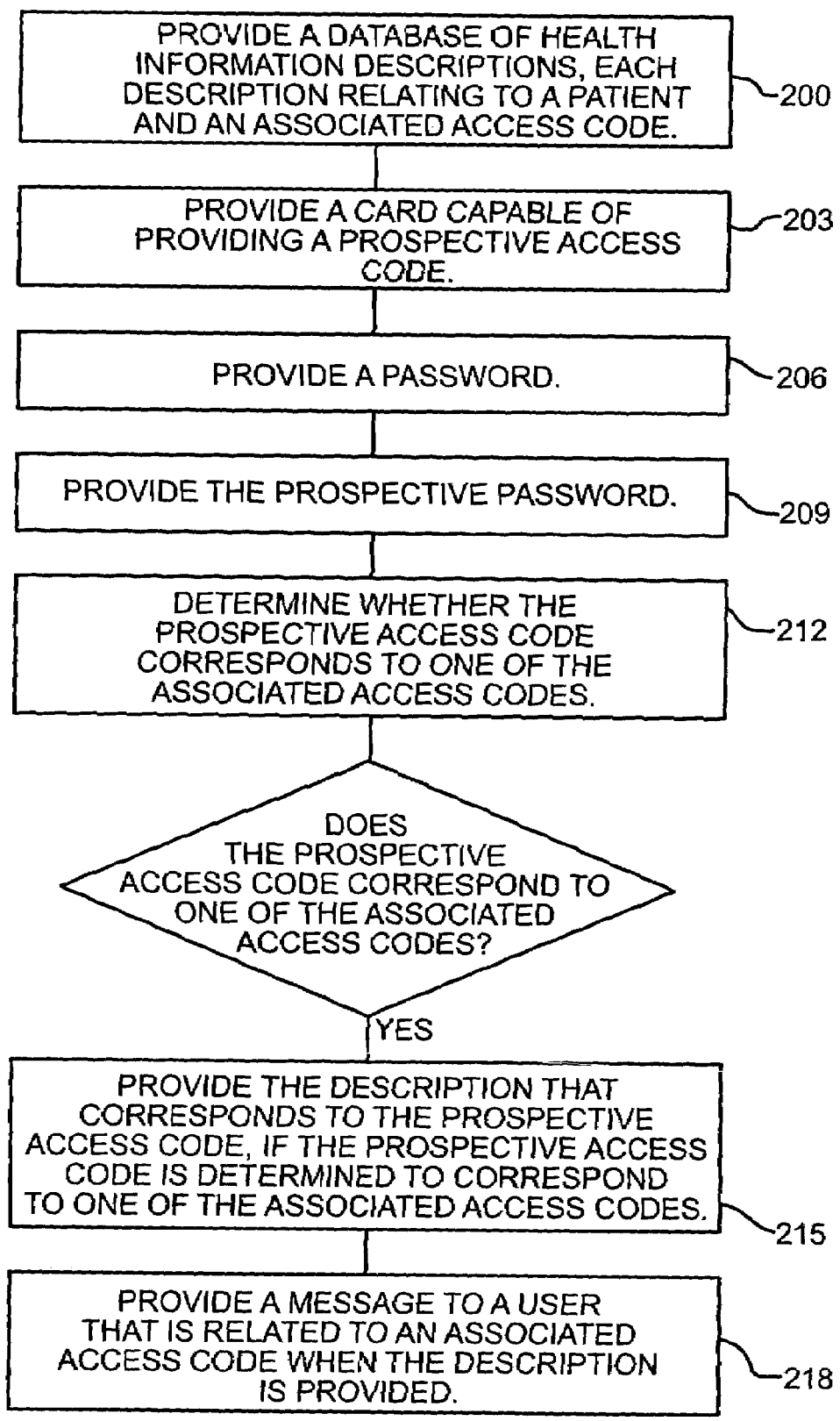
FIG. 3 is a flow chart illustrating a method according to the invention.

In one embodiment of the method, a card having a card code corresponding to the prospective access code may be provided. Once the card code is read, the prospective access code may be provided. In one method of the present invention, a user must enter a password before the prospective access code is provided. See FIG. 3. In another embodiment of the method, a fingerprint having a pattern is read, and the pattern is provided in the form of a prospective access code. In another embodiment of the method, a retina is read and the pattern on the retina is provided in the form of a prospective access code.

The method may include receiving a change to a description. Once a change is received, the description may be updated to reflect the change. The method may include recording who made the change.

A method according to the present invention may issue one or more access codes. For example, one of the associated pairs may be issued to one of the patients, and that associated pair may be related only to the description of that patient. As another example, one of the associated pairs may be issued to a physician, and that associated pair may be related to a plurality of the descriptions corresponding to the physician's patients.

As a third example, an associated pair may be issued to a health care provider, and related to a plurality of descriptions corresponding to patients to whom the health care provider provides services. As a fourth example, an associated pair may be issued to a medical cost payer, and related to a plurality of descriptions corresponding to patients for whom the medical cost payer provides services.

In an embodiment of the invention, a message may be provided 112 to a user, such as a patient, physician, health care provider or medical cost payer when a patient's description is provided. In this manner, users can keep track of when and who is accessing his/her description.

The invention includes an article of manufacture 31. The article of manufacture 31 may be a computer usable medium, such as a CD ROM, random access memory or read only memory. The computer usable medium has computer readable program code instructions embodied therein to cause a computer to provide access to medical information. The instructions may have one or more computer readable program code modules to (1) determine whether a prospective pair is among a group of associated pairs, and (2) if the prospective pair is among the group of associated pairs, provide medical information corresponding to the prospective pair.

The article of manufacture 31 may also include a computer readable program code module to instruct a computer to change the provided medical information, and may further include a computer readable program code module to record who made the change to the provided medical information. In addition, the article of manufacture 31 may include a computer readable program code module to instruct a computer to provide a message to a patient when the description relating to the patient is provided.

Although the invention has been described with respect to one or more particular embodiments, it will be understood that other embodiments of the invention may be made without departing from the spirit and scope of the invention.

What is claimed is:

1. A medical information system, comprising:
   a database of health information descriptions, each description relating to a patient and an associated pair, the associated pair comprising an associated access code, which is associated with the patient, and an associated password, which is associated with a non-patient user of the system;
   a computer readable memory on a portable card, the memory having stored therein a prospective access code, which is associated with a patient;
   a first computer programmed to provide a prospective pair substantially simultaneously, the prospective pair comprising the prospective access code and a prospective password, the prospective password being associated with a user of the system;
   a second computer, in communication with the database and with the first computer, the second computer being programmed to determine whether the prospective pair corresponds to the associated pair, and if the prospective pair is determined to correspond to the associated pair, then the second computer provides only the description that corresponds to the prospective pair; and further the first computer is programmed to provide a change to one of the descriptions; and the second computer is programmed to receive the change to the one of the descriptions, and then modify the database to reflect the change and the second computer is programmed to record who made the change to the one of the descriptions.

2. The system of claim 1, further comprising a card having thereon a card code corresponding to the prospective access code.

3. The system of claim 1, wherein the prospective password is a fingerprint.

4. The system of claim 1, wherein the prospective password is a retinal scan.

5. The system of claim 1, wherein one of the associated pairs is issued to one of the patients, and the description corresponding to the one of the patients is related to the one of the associated pairs.

6. The system of claim 1, wherein one of the associated pairs is issued to a physician, and the one of the associated pairs is related to a plurality of descriptions.

7. The system of claim 1, wherein one of the associated pairs is issued to a health care provider, and the one of the associated pairs is related to a plurality of descriptions.

8. The system of claim 1, wherein one of the associated pairs is issued to a medical cost payer, and the one of the associated pairs is related to a plurality of descriptions.

9. The system of claim 1, wherein the second computer is programmed to cause a message to be sent to a user of the system, the user being related to an associated pair.

10. A computer implemented method of providing medical information, comprising:
   providing a computer database of health information descriptions, each description relating to a patient and an associated pair, each associated pair comprising an associated access code, which is associated with the patient, and an associated password, which is associated with a non-patient user of the system;
   receiving a prospective pair, the prospective pair comprising a prospective access code, which is associated with a patient and provided substantially simultaneously by a computer readable memory on a portable card, and a prospective password, which is associated with a user of the system;
   determining whether the prospective pair corresponds to one of the associated pairs;
   if the prospective pair is determined to correspond to one of the associated pairs, then providing only the description that corresponds to the prospective pair;
   receiving a change to the provided description, and modifying the database according to the change; and
   recording who made the change to the provided description.

11. The method of claim 10, further comprising reading a card having thereon a card code corresponding to the prospective access code.

12. The method of claim 10, further comprising reading a fingerprint having thereon a pattern corresponding to the prospective password.

13. The method of claim 10, further comprising reading a retina having thereon a pattern corresponding to the prospective password.

14. The method of claim 10, further comprising issuing one of the associated pairs to one of the patients, and relating the one of the associated pairs with only the description relating to the one of the patients.

15. The method of claim 10, further comprising issuing one of the associated pairs to a physician, and relating the one of the associated pairs to a plurality of the descriptions.

16. The method of claim 10, further comprising issuing one of the associated pairs to a health care provider, and relating the one of the associated pairs to a plurality of the descriptions.

17. The method of claim 10, further comprising issuing one of the associated pairs to a medical cost payer, and relating the one of the associated pairs to a plurality of the descriptions.

18. The method of claim 10, further comprising providing a message to a user related to an associated pair when the description is provided.

19. An article of manufacture comprising a computer usable medium having computer readable program code instructions embodied therein to cause a computer to provide access to medical information, the instructions having:
   a computer readable program code module to determine whether a substantially simultaneously submitted prospective pair is among a group of associated pairs, each associated pair having (a) an access code which is associated with a patient corresponding to the medical information, and (b) a password associated with a non-patient user of the system;
   a computer readable program code module to provide only medical information corresponding to the prospective pair, if the prospective pair is among the group of associated pairs; and further comprising
   a computer readable program code module to instruct a computer to change the provided medical information; and
   a computer readable program code module to instruct a computer to record who made the change to the provided medical information.

20. The article of manufacture of claim 19, further comprising a computer readable program code module to instruct a computer to provide a message to a user related to an associated pair when the description is provided.

21. A medical information system, comprising:
   a database of health information descriptions, each description relating to a patient and an associated access code, and wherein the associated access code has at least two acceptable passwords associated with it, wherein at least one of the acceptable passwords corresponds to a non-patient user of the system and is associated with the prospective access code;
   a portable card having thereon a first computer programmed to provide a prospective access code upon entry of at least one acceptable password;
   a second computer, in communication with the data base and with the first computer, the second computer being programmed to determine whether the prospective access code corresponds to one of the associated access codes, and if the prospective access code is determined to correspond to one of the associated access codes, then the second computer provides only the description that corresponds to the prospective access code;
   wherein the first computer is programmed to provide a change to one of the descriptions, the second computer is programmed to receive the change to the one of the descriptions, and then modify the database to reflect the change, and the second computer is programmed to record who made the change to the one of the descriptions.

22. The system of claim 21, wherein the prospective password is a fingerprint.

23. The system of claim 21, wherein the prospective password is a retinal scan.

24. The system of claim 21, wherein one of the associated access codes is issued to one of the patients, and the description corresponding to the one of the patients is related to the one of the associated access codes.

25. The system of claim 21, wherein one of the associated access codes is issued to a physician, and the one of the associated access codes is related to a plurality of descriptions.

26. The system of claim 21, wherein one of the associated access codes is issued to a health care provider, and the one of the associated access codes is related to a plurality of descriptions.

27. The system of claim 21, wherein one of the associated access codes is issued to a medical cost payer, and the one of the associated access codes is related to a plurality of descriptions.

28. The system of claim 21, wherein the second computer is programmed to cause a message to be sent to a user of the system, the user being related to the provided description.

29. A method of providing medical information, comprising:
providing a database of health information descriptions, each description relating to a patient and an associated access code, wherein the associated access code has at least two acceptable passwords associated with it, wherein at least one of the acceptable passwords corresponds to a non-patient user of the system and is associated with the prospective access code;
providing a portable card having thereon a computer readable memory capable of providing a prospective access code upon entry of at least one acceptable password;
providing a password;
determining whether the password is among a group of acceptable passwords that are associated with the prospective access code, at least one of the passwords being associated with an entity other than the patient;
providing the prospective access code;
determining whether the prospective access code corresponds to one of the associated access codes;
if the prospective access code is determined to correspond to one of the associated access codes, then providing only the description that corresponds to the prospective access code;
receiving a change to the provided description, and modifying the database according to the change;
recording who made the change to the provided description.

30. The method of claim 29, wherein providing a password includes providing a fingerprint having thereon a pattern corresponding to the password.

31. The method of claim 29, wherein providing a password includes providing a retina having thereon a pattern corresponding to the password.

32. The method of claim 29, further comprising issuing one of the associated access codes to one of the patients, and relating the one of the associated access codes with only the description relating to the one of the patients.

33. The method of claim 29, further comprising issuing one of the associated access codes to a physician, and relating the one of the associated access codes to a plurality of the descriptions.

34. The method of claim 29, further comprising issuing one of the associated access codes to a health care provider, and relating the one of the associated access codes to a plurality of the descriptions.

35. The method of claim 29, further comprising issuing one of the associated access codes to a medical cost payer, and relating the one of the associated access codes to a plurality of the descriptions.

36. The method of claim 29, further comprising providing a message to a user related to an associated access code when the description is provided.

37. An article of manufacture comprising a computer usable medium having computer readable program code instructions embodied therein to cause a computer to provide access to medical information of a patient, the information being accessible by substantially simultaneously providing an associated pair, the associated pair comprising an associated access code and an associated password, the instructions having:
a computer readable program code module to determine whether a prospective access code is among a group of associated access codes, and whether a prospective password is among a group of associated passwords, wherein at least one of the associated access codes corresponds to the patient, and wherein the associated password corresponds to an entity that is not the patient;
a computer readable program code module to provide only medical information corresponding to both the prospective access code and the prospective password, if the prospective access code is among the group of associated access codes and the prospective password is among the group of associated passwords; and further comprising
a computer readable program code module to instruct a computer to change the provided medical information; and
a computer readable program code module to instruct a computer to record who made the change to the provided medical information.

38. The article of manufacture of claim 37, further comprising a computer readable program code module to instruct a computer to provide a message to a user related to an associated access code when the description is provided to someone other than the user.

* * * * *